(12) United States Patent
Shiozawa (10) Patent No.: US 12,306,117 B2
(45) Date of Patent: May 20, 2025

(54) METHOD OF EVALUATING CONCENTRATION OF SULFUR

(71) Applicant: SUMITOMO RUBBER INDUSTRIES, LTD., Kobe (JP)

(72) Inventor: Tomomi Shiozawa, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 0 days.

(21) Appl. No.: 18/513,040

(22) Filed: Nov. 17, 2023

(65) Prior Publication Data

US 2024/0183803 A1 Jun. 6, 2024

(30) Foreign Application Priority Data

Dec. 2, 2022 (JP) .................................. 2022-193528

(51) Int. Cl.
*G01N 23/202* (2006.01)
*G01N 33/44* (2006.01)

(52) U.S. Cl.
CPC ......... *G01N 23/202* (2013.01); *G01N 33/445* (2013.01); *G01N 2223/054* (2013.01); *G01N 2223/615* (2013.01)

(58) Field of Classification Search
CPC ............... G01N 23/202; G01N 33/445; G01N 2223/054; G01N 2223/615
See application file for complete search history.

(56) References Cited

U.S. PATENT DOCUMENTS

| 2018/0113182 A1* | 4/2018 | Masui | G01N 23/005 |
| 2019/0285609 A1* | 9/2019 | Kaneko | G01N 33/445 |
| 2023/0273181 A1* | 8/2023 | Iwasaki | G01N 21/314 |
| | | | 436/123 |

FOREIGN PATENT DOCUMENTS

EP 3098596 A1 * 11/2016 ............ C08F 212/08

OTHER PUBLICATIONS

Bunyatova, "Free radicals and polarized targets," Nuclear Instruments and Methods in Physics Research A, vol. 526, 2004, pp. 22-27.
Kumada et al., "Dynamic nuclear polarization of high- and low-crystallinity polyethylenes," Nuclear Instruments and Methods in Physics Research A, vol. 606, 2009, pp. 669-674.
Kumada et al., "Dynamic nuclear polarization system for the SANS-J-II spectrometer at JAEA," Physica B, vol. 404, 2009, pp. 2637-2639.
Kumada et al., "Mesoscale spatial distribution of electron spins studied by time-resolved small-angle and ultrasmall-angle neutron scattering with dynamic nuclear polarization: A case of 2,2,6,6-tetramethylpiperidine 1-oxyl (TEMPO) doped in high-density polyethylene," The Journal of Chemical Physics, vol. 133 No. 054504, 2010, 8 pages total.

(Continued)

*Primary Examiner* — Mark R Gaworecki
(74) *Attorney, Agent, or Firm* — Birch, Stewart, Kolasch & Birch, LLP (57) ABSTRACT

Provided is a method of evaluating a concentration of sulfur in a polymer composite material. The present disclosure relates to a method of evaluating a concentration of sulfur in a polymer composite material by small-angle neutron scattering with $^1$H dynamic nuclear spin polarization.

4 Claims, 3 Drawing Sheets

(56) References Cited

OTHER PUBLICATIONS

Noda et al., "Inhomogeneous dynamic nuclear polarization of protons in a lamella-forming diblock copolymer investigated by a small-angle neutron scattering method," Journal of Applied Crystallography, vol. 44, 2011, pp. 503-513.
Noda et al., "Small-angle neutron scattering study of dynamically polarized polyethylenes," Physica B, vol. 404, 2009, pp. 2572-2574.
Takenaka et al., "Structure Analyses of Swollen Rubber-Filler Systems by Using Contrast Variation SANS," Macromolecules, vol. 42, No. 1, 2009, pp. 308-311.

\* cited by examiner

METHOD OF EVALUATING CONCENTRATION OF SULFUR

TECHNICAL FIELD

The present disclosure relates to a method of evaluating the concentration of sulfur.

BACKGROUND ART

Contrast variation neutron scattering is a dominant technique for the structural analysis of multicomponent systems such as polymer composite materials (Non-Patent Literature 1). This technique utilizes the difference in contrast between protium and deuterium, which is the peculiar nature of neutron scattering, to analyze polymer composite materials. Solvent contrast variation neutron scattering involves swelling a polymer composite material in mixtures of a protium solvent and a deuterium solvent in varied ratios as swelling solvents, and performing neutron scattering measurements on each sample, thereby carrying out the structural analysis of the multicomponent system.

Methods reported these days involve a structural analysis of a multicomponent system using a technique known as $^1$H dynamic nuclear polarization contrast variation neutron scattering (Non-Patent Literatures 2 to 7). In this technique, a paramagnetic radical is introduced into a material, and then the material is irradiated with microwaves at an extremely low temperature under a magnetic field to polarize the proton spins in the material. Thus, the contrast can be changed, enabling structural analysis of the multicomponent system.

While the conventional methods can analyze a sample that includes portions with non-uniform polymer concentrations formed by crosslinking, quantifying the concentration of sulfur in the portions with non-uniform polymer concentrations is difficult due to variations in composition throughout the sample.

CITATION LIST

Non-Patent Literature

Non-Patent Literature 1: Macromolecules, 42, 308-311 (2009)
Non-Patent Literature 2: Nucl. Inst. Meth. A 526, 22-27 (2004)
Non-Patent Literature 3: Physica B 404 2572-2574 (2009)
Non-Patent Literature 4: Physica B 404 2637-2639 (2009)
Non-Patent Literature 5: Nucl. Inst. Meth. A 606, 669-674 (2009)
Non-Patent Literature 6: J. Chem. Phys. 133, 054504 (2010)
Non-Patent Literature 7: J. Appl. Cryst. 44. 503-513 (2011)

SUMMARY OF INVENTION

Technical Problem

The present disclosure aims to solve the above problem and to provide a method of evaluating a concentration of sulfur in a polymer composite material.

Solution to Problem

The present disclosure relates to a method of evaluating a concentration of sulfur in a polymer composite material by small-angle neutron scattering with $^1$H dynamic nuclear spin polarization.

Advantageous Effects of Invention

The present disclosure provides a method of evaluating a concentration of sulfur in a polymer composite material by small-angle neutron scattering with $^1$H dynamic nuclear spin polarization. This method can evaluate the concentration of sulfur in a polymer composite material.

DESCRIPTION OF EMBODIMENTS

The present disclosure relates to a method of evaluating a concentration of sulfur in a polymer composite material by small-angle neutron scattering with $^1$H dynamic nuclear spin polarization.

For example, the structural analysis in one conventional technique requires immersion in at least three types of solution mixtures with different deuteride concentrations and therefore requires three nanocomposites. This technique may cause errors derived from a potential variation in the compositions of the nanocomposites or a variation in the degree of swelling in the solvent swelling.

In contrast, when small-angle neutron scattering with $^1$H dynamic nuclear spin polarization is combined with solvent swelling as in the present disclosure, one nanocomposite is immersed in a deuterated solvent and subjected to $^1$H dynamic nuclear spin polarization, thus causing no error derived from position dependence of the nanocomposite and the degree of swelling. It is therefore possible to accurately extract information on a substance which is usually contained in an amount of only about 1% by mass in a cross-linked rubber, such as sulfur.

Moreover, the present disclosure permits a very large difference, for example a 10-fold difference, in contrast between sulfur and a polymer.

Accordingly, the present disclosure can accurately measure the concentration level of sulfur in a sample.

The present disclosure relates to a method of measuring or evaluating the concentration of sulfur in a polymer composite material (sample) by small-angle neutron scattering with $^1$H dynamic nuclear spin polarization. Here, the term "small-angle neutron scattering with $^1$H dynamic nuclear spin polarization" refers to a technique of small-angle neutron scattering performed on a sample which is under $^1$H dynamic nuclear spin polarization conditions.

Small-angle neutron scattering with $^1$H dynamic nuclear spin polarization changes the scattering length density of a material with protons in the sample, whereby the difference in contrast between the material with protons and a material with no proton can be improved. The improvement enables the analysis of the diffusion of filler such as carbon black, or zinc, sulfur, etc. in multi-component samples such as rubber compositions. In particular, the present disclosure evaluates the concentration of sulfur.

The term "$^1$H dynamic nuclear spin polarization" refers to a technique that involves applying a strong magnetic field and a microwave to radical species with electron spin to transfer electron spin polarization to nuclear spin polarization, thereby obtaining a degree of nuclear spin polarization equivalent to that of electron spin polarization.

Small-angle neutron scattering (hereinafter, also referred to as SANS) is a small-angle neutron scattering analysis (scattering angle: usually 10 degrees or less) to measure scattering intensities by irradiating a sample with neutrons. In small-angle neutron scattering, structural information of a substance can be obtained by measuring the neutrons with small scattering angles among neutrons scattered by the irradiation of the substance with neutrons. Based on the information, inhomogeneities on the order of a few nanometers, such as microphase-separated structures, in cross-linked rubbers can be analyzed.

The neutron flux intensity, the method, the apparatuses, and the like used in SANS analysis may suitably be those described in JP 2014-102210 A, which is hereby incorporated by reference in its entirely. SANS analysis is excellent in terms of contrast.

SANS analysis is performed in a region q defined by Expression (1) below.

In SANS analysis, scattered neutrons are detected by a neutron detector, and then an image is generated by an image processor or the like using the neutron detection data from the neutron detector.

$$q = \frac{4\pi \sin(\theta/2)}{\lambda} \quad \text{Expression (1)}$$

In Expression (1), $\theta$ denotes the scattering angle, and $\lambda$ denotes the wavelength of X-rays or neutrons.

Examples of usable neutron detectors include two-dimensional detectors such as X-ray films, nuclear dry plates, X-ray image pick-up tubes, X-ray fluorescent amplifiers, X-ray image intensifiers, X-ray imaging plates, X-ray CCDs, and X-ray amorphous materials, and line sensor one-dimensional detectors.

The image processor may be appropriately selected from known image processors which can generate neutron scattering images.

The polymer composite material applicable in the present disclosure is a material (composition) in which various additives are blended with a polymer material.

Non-limiting examples of the polymer material include diene-based rubbers containing a hydrogen atom in the molecular skeleton, such as natural rubber (NR), polyisoprene rubber (IR), polybutadiene rubber (BR), styrene-butadiene rubber (SBR), styrene-isoprene-butadiene rubber (SIBR), ethylene-propylene-diene rubber (EPDM), chloroprene rubber (CR), acrylonitrile-butadiene rubber (NBR), and butyl rubber (IIR). Diene-based rubbers are preferred, and styrene-butadiene rubber is more preferred among these. The polymer material may be used alone or in combinations of two or more.

Examples of the various additives include fillers such as silica and carbon black, zinc oxide, and vulcanizing agents such as sulfur.

The amount of the additives is not limited. The amount of fillers per 100 parts by mass of the polymer material (matrix polymer) is preferably 5 to 150 parts by mass, more preferably 10 to 100 parts by mass. The amount of sulfur per 100 parts by mass of the polymer material (matrix polymer) is preferably 0.1 to 10 parts by mass, more preferably 0.3 to 5 parts by mass, still more preferably 0.5 to 3 parts by mass.

Examples of sulfur include those commonly used in the rubber industry, such as powdered sulfur, precipitated sulfur, colloidal sulfur, insoluble sulfur, highly dispersible sulfur, and soluble sulfur. These may be used alone or in combinations of two or more. Usable commercial products are available from Tsurumi Chemical Industry Co., Ltd., Karuizawa sulfur Co., Ltd., Shikoku Chemicals Corporation, Flexsys, Nippon Kanryu Industry Co., Ltd., Hosoi Chemical Industry Co., Ltd., etc.

Preferably, a cross-linked rubber is used as the polymer composite material.

The thickness of the polymer composite material is not limited. To prevent the temperature rise during microwave irradiation in a dynamic nuclear spin polarization experiment, the thickness is preferably 3 mm or less, more preferably 2 mm or less, still more preferably 1 mm or less. The lower limit of the thickness is not limited. A thin polymer composite material causes no problem.

The polymer composite material is preferably doped with a paramagnetic radical compound.

Non-limiting examples of the paramagnetic radical compound dispersed in the polymer composite material include 2,2,6,6-tetramethylpiperidine 1-oxyl (TEMPO), 4-oxo-2,2,6,6-tetramethylpiperidine N-oxyl (TEMPONE), 1-oxyl-2,2,6,6-tetramethyl-4-hydroxypiperidine (TEMPOL), and trityl radical. Of these, 2,2,6,6-tetramethylpiperidine 1-oxyl (TEMPO) is preferred.

For efficient $^1$H dynamic nuclear polarization, electron spins are required to be uniformly diffused at an appropriate concentration. For example, the optimal concentration in experiments directed to pure polymer materials is 50 mM. In the polymer composite material, however, no radical can penetrate into fillers such as silica and carbon black, and therefore the distance between radicals is shorter than that expected from the net radical concentration measured by electron spin resonance spectroscopy (ESR). Taking this issue into consideration, the local concentration of the paramagnetic radical compound is defined by the following expression.

(Local concentration of paramagnetic radical compound)=(Concentration of paramagnetic radical compound)/(1−(Volume fraction of filler))

To obtain a favorable degree of $^1$H nuclear spin polarization, the local concentration of the paramagnetic radical compound in the polymer composite material is preferably 10 mM or more, more preferably 30 mM or more, still more preferably 50 mM or more, while it is preferably 80 mM or less, more preferably 70 mM or less.

In the polymer composite material, preferably, the local concentration of the paramagnetic radical compound is substantially not position-dependent. That is, the local concentration of the paramagnetic radical compound in the polymer composite material is preferably substantially uniform. Specifically, when the local concentration of the paramagnetic radical compound is measured at 10 points per polymer composite material, the difference in the local concentration of the paramagnetic radical compound between a region with the highest local concentration and a region with the lowest local concentration is preferably 1 mM or less, more preferably 0.5 mM or less, further preferably 0.1 mM or less, particularly preferably 0.05 mM or less.

The polymer composite material is preferably doped with a deuterated solvent.

Examples of the deuterated solvent (heavy solvent) include deuterated toluene, deuterated hexane, deuterated chloroform, and deuterated methanol. Deuterated toluene is preferred among these.

To allow the contrast of the matrix polymer to match the contrasts of other components in the polymer composite material, the amount of the deuterated solvent relative to the amount of the polymer material (matrix polymer) in the polymer composite material is preferably 0.5 to 200%, more preferably 10 to 100%.

In view of experimental data analysis, the degree of $^1H$ nuclear spin polarization of the polymer composite material is preferably 50% or higher, more preferably 55% or higher, still more preferably 60% or higher, while it is preferably 70% or lower, more preferably 65% or lower.

The degree of $^1H$ nuclear spin polarization of the polymer composite material is defined by the following expression and can be measured by, for example, the following method.

(Degree of $^1H$ nuclear spin polarization)=(Number of up-spins−Number of down-spins)/(Number of up-spins+Number of down-spins)

$^1H$ Dynamic Nuclear Spin Polarization

When the degree of $^1H$ nuclear spin polarization is measured under thermal equilibrium conditions at a temperature of 4.2 [K] and a magnetic field strength of 6.7 [Tesla], the degree of $^1H$ nuclear spin polarization is theoretically 0.163%. The peak area of an NMR signal in predetermined conditions is used as a reference, and the degree of $^1H$ nuclear spin polarization is estimated from the rate of increase in the peak area of the NMR signal at a temperature of 1.2 [K] and a magnetic field strength of 6.7 [Tesla] under microwave irradiation (frequency: 188 [GHz]).

The polymer composite material preferably contains substantially no molecular oxygen. The polymer composite material containing substantially no molecular oxygen can be suitably produced by introducing (dispersing) a paramagnetic radical compound and a deuterated solvent into the polymer composite material under conditions where no oxygen is present as described below.

The polymer composite material can be produced as follows: first, a polymer material is kneaded with additives such as sulfur and fillers in a kneading apparatus such as a Banbury mixer, a kneader, or an open roll mill, subsequently the kneaded mixture is subjected to a crosslinking reaction (vulcanization) to give a polymer composite material, and then a paramagnetic radical compound and a deuterated solvent are diffused into the polymer composite material to dope the polymer composite material with the paramagnetic radical compound and the deuterated solvent.

In particular, the method preferably includes the step of dispersing a paramagnetic radical compound and a deuterated solvent in a polymer composite material in the presence of an inert gas, or under vacuum, or while immersing the polymer composite material in a solvent. This step removes molecular oxygen present in the polymer composite material, so that the distance between radicals in the polymer composite material can be optimized, thereby providing a polymer composite material having a higher degree of $^1H$ nuclear spin polarization than those in prior arts. Specifically, a polymer composite material containing substantially no molecular oxygen can be suitably produced by doping a polymer composite material with a paramagnetic radical compound and a deuterated solvent in oxygen-free conditions. In the produced polymer composite material which contains substantially no molecular oxygen, the local concentration of the paramagnetic radical compound is substantially not position-dependent. Accordingly, it is possible to provide a polymer composite material having a higher degree of $^1H$ nuclear spin polarization than those in prior arts.

Non-limiting examples of a specific method of dispersing a paramagnetic radical compound and a deuterated solvent in a polymer composite material in the presence of an inert gas, or under vacuum, or while immersing the polymer composite material in a solvent include dispersing a paramagnetic radical compound and a deuterated solvent in a polymer composite material in a deoxygenated environment (in the presence of an inert gas, under vacuum, or in a solvent), such as in a glove box (for example, a glove box with a molecular oxygen concentration of 1 ppm or less), or in an environment where oxygen has been removed by a deoxygenating agent.

Examples of the inert gas include nitrogen, argon, and helium.

Examples of the solvent include toluene, tetrahydrofuran, benzene, methacrylic acid, methyl methacrylate, butyl methacrylate, styrene, and xylene.

The dispersion of a paramagnetic radical compound and a deuterated solvent may be carried out by any method, such as vapor infiltration or immersion into a mixed solution of the paramagnetic radical compound and the deuterated solvent. Vapor infiltration may be carried out, for example, by standing under deoxygenated conditions at 20° C. to 60° C. for 3 to 14 days, preferably 5 to 14 days. Such a long-term standing more suitably enables the production of a polymer composite material in which the local concentration of the paramagnetic radical compound is substantially not position-dependent and thus has a higher degree of $^1H$ nuclear spin polarization than those in prior arts.

When a sample (polymer composite material) is subjected to small-angle neutron scattering with $^1H$ dynamic nuclear spin polarization, the degree of $^1H$ nuclear spin polarization $P_H$ of the sample is changed by dynamic nuclear spin polarization. The resulting $P_H$ value is multiplied by the degree of polarization of incident neutrons $P_N$ to give a degree of spin polarization $P_H P_N$.

Here, $P_H P_N$ can be obtained as described below.

First, the polymer composite material as a measurement sample is prepared by the following method.

Preparation of Sample

Materials including 100 parts by mass of styrene-butadiene rubber (JSR Corporation), 1.6 parts by mass of sulfur (powdered sulfur, Tsurumi Chemical Industry Co., Ltd.), 1.8 parts by mass of a vulcanization accelerator (NOCCELER NS (N-tert-butyl-2-benzothiazylsulfenamide), Ouchi Shinko Chemical Industrial Co., Ltd.), and 1.0 parts by mass of a vulcanization accelerator (NOCCELER D (1,3-diphenylguanidine), Ouchi Shinko Chemical Industrial Co., Ltd.) are kneaded with an open roll mill, and the resulting kneaded mixture is vulcanized to obtain a cross-linked rubber.

The cross-linked rubber is sliced to a thickness of 1 mm and then cut into a 7 mm×8 mm piece, whereby a sample is prepared.

Subsequently, a paramagnetic radical compound and a deuterated solvent are introduced into the prepared sample by the method described below to prepare a measurement sample for small-angle neutron scattering with $^1$H dynamic nuclear spin polarization.

Preparation of Solution Mixture

Paramagnetic radical TEMPO (2,2,6,6-tetramethylpiperidine 1-oxyl) is added to deuterated toluene and mixed to obtain a solution mixture. The concentration of the TEMPO in the solution mixture is 12 mg/ml.

Introduction of Paramagnetic Radical Compound and Deuterated Solvent

The sample and the solution mixture obtained above are placed in a vial such that the cross-linked rubber (sample slice) is completely immersed in the solution mixture, followed by standing still under a deoxygenated environment all day and night (about one day). Thus, the paramagnetic radical compound and the deuterated solvent are introduced into the sample, thereby obtaining a measurement sample.

Next, the measurement sample prepared with the below-described apparatus and conditions is subjected to small-angle neutron scattering with $^1$H dynamic nuclear spin polarization to vary the degree of $^1$H nuclear spin polarization $P_H$ in the measurement sample by dynamic nuclear spin polarization. The degree of polarization of incident neutrons $P_N$ is $-0.93$, and this value is multiplied by the degrees of $^1$H nuclear spin polarization $P_H$ in the sample to give $P_H P_N$ values of $-63.7\%$, $-40.6\%$, $-31.0\%$, $-0.7\%$, $-10.3\%$, $+29.0\%$, $+43.9\%$, and $+56.9\%$. $P_H P_N$ indicates the degree of spin polarization.

<Small-Angle Neutron Scattering With $^1$H Dynamic Nuclear Spin Polarization>
  ($^1$H dynamic nuclear spin polarization apparatus)
    Dynamic proton nuclear spin polarizer attached to IBARAKI materials design diffractometer
    Cryostat: product of JASTEC
    Magnetic field strength: 6.7 [Tesla]
    Experimental temperature: 1.2 K
    Microwave frequency: 188 [GHz]
  (SANS analysis)
    Apparatus: IBARAKI materials design diffractometer (iMATERIA) in J-PARC
    Incident neutrons: polarized neutrons
    (Degree of polarization $P_N$ of polarized neutrons=−0.93)
    Measurement wave number q: $0.005<q<0.3$ (Å$^{-1}$)
    Wavelength of incident neutrons: 0.2 to 10 Å
    MLF beam: 700 kW For example, in a sample containing styrene-butadiene rubber with protons, the scattering length density of the styrene-butadiene rubber can be changed by changing the degree of spin polarization $P_H P_N$ as follows.
  Styrene-butadiene rubber: $(0.62+8.39\ P_H P_N)\times 10^{10}$ (cm$^{-2}$)

In contrast, in a sample with no proton, the scattering length density does not change when the degree of spin polarization $P_H P_N$ is changed as follows.
  Sulfur: $1.08\times 10^{10}$ (cm$^{-2}$)
  Deuterated toluene: $5.66\times 10^{10}$ (cm$^{-2}$)

Figure 1:
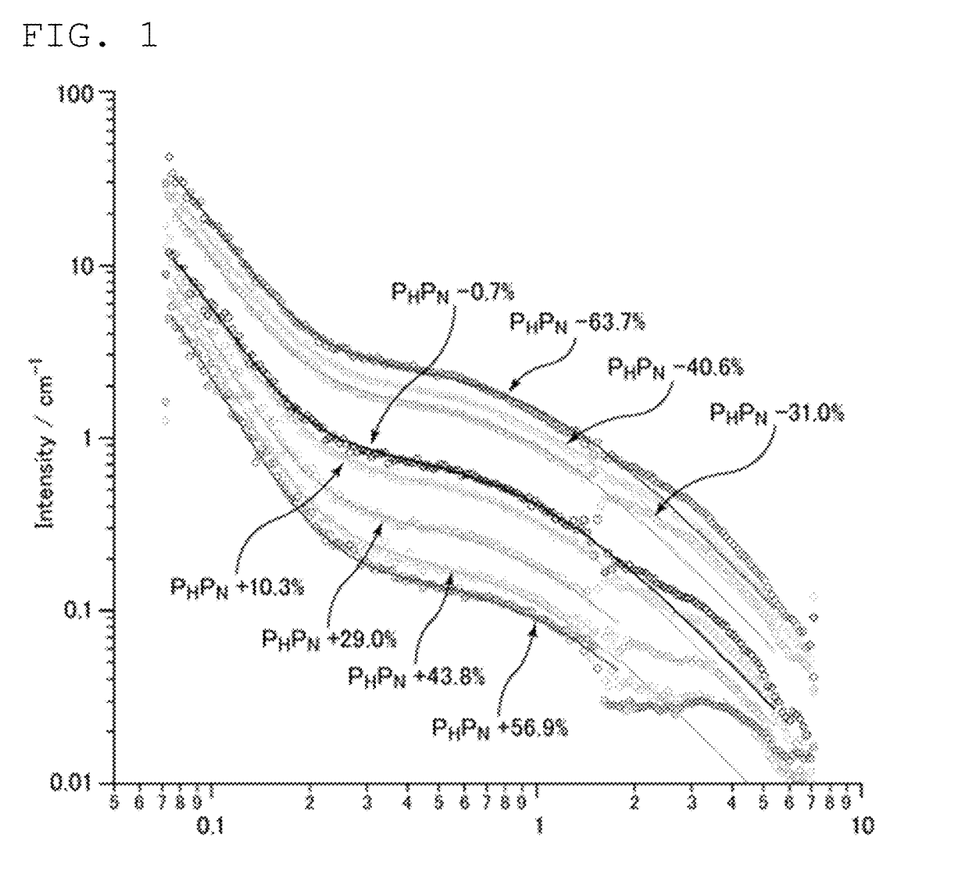
FIG. 1 shows scattering intensity curves I(q) of a measurement sample.

The background of an empty cell is subtracted from the measurement result, and then the thickness is corrected, whereby scattering intensity curves I(q) as shown in FIG. 1 can be obtained.

A model analysis of each scattering intensity curve I(q) is performed using the following Expression (1), which is a combination of the Debye-Buche equation and the Ornstein-Zernike equation, with an assumed size $\Xi$ of a densely cross-linked part and an assumed size $\xi$ of a cross-linked network.

$$I(q)=A_{DB}/(1+q^2\Xi^2)^2+A_{OZ}/(1+q^2\xi^2) \quad (1)$$

In Expression (1), q denotes the wave number (Å$^{-1}$), $\Xi$ denotes the size of a densely cross-linked part, and $\xi$ denotes the size of a cross-linked network.

By fitting the scattering intensity curve I(q) using the model analysis, $A_{DB}$, $A_{OZ}$, the size $\Xi$ of a densely cross-linked part, and the size $\xi$ of a cross-linked network are obtained.

Here, the size $\Xi$ of a densely cross-linked part and the size $\xi$ of a cross-linked network do not depend on the degree of polarization.

Figure 2A:
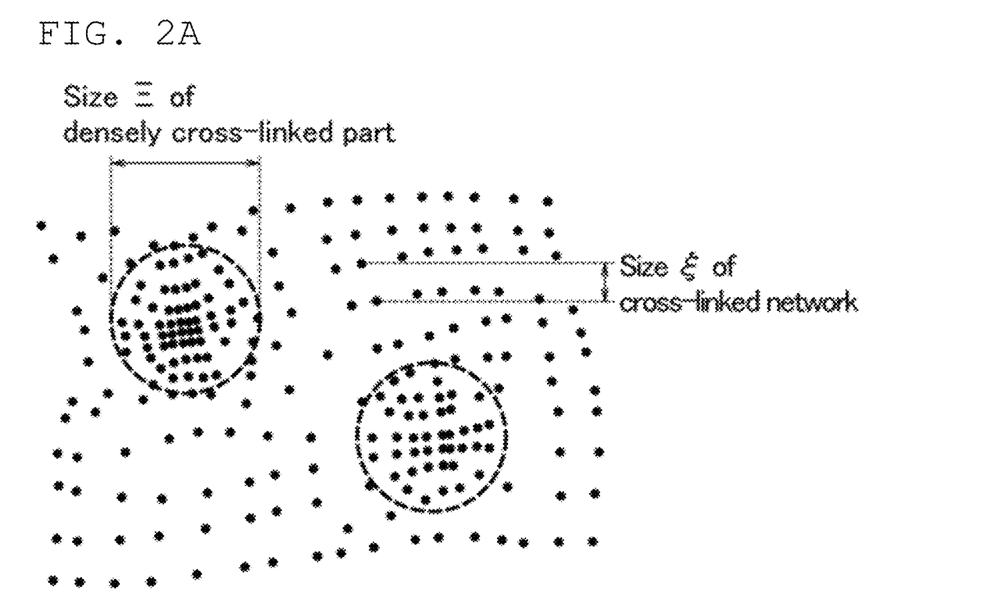
FIGS. 2A and 2B show schematic diagrams schematically illustrating non-uniform crosslinking parts of a cross-linked rubber.
Figure 2B:
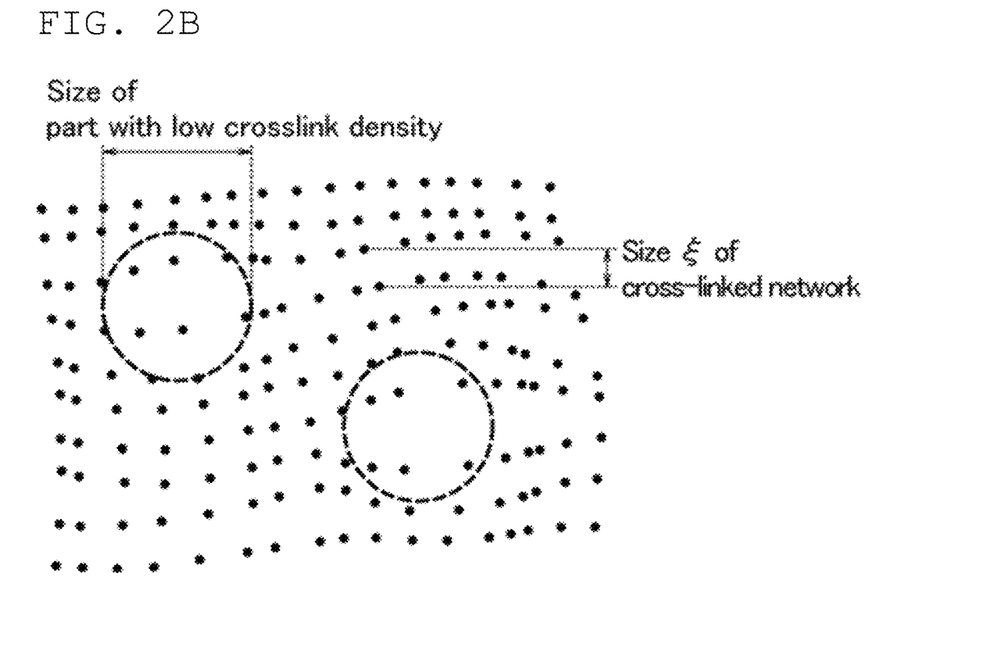

The term "densely cross-linked part" refers to a part of a cross-linked rubber where the crosslink density in the rubber matrix of the cross-linked rubber is high as illustrated in FIG. 2A among non-uniform crosslinking parts of the cross-linked rubber as schematically illustrated in FIGS. 2A and 2B. The densely cross-linked part does not include a part with a low crosslink density as illustrated in FIG. 2B. For example, the densely cross-linked part may be a part of rubber where the degree of swelling of the rubber is locally lower than the degree of swelling of the bulk rubber. The term "size $\Xi$ of the densely cross-linked part" refers to the size of such a part with a high crosslink density. The size $\Xi$ can be measured by the method described in JP 2016-223806 A, which is hereby incorporated by reference in its entirely.

The term "size $\Xi$ of a cross-linked network" refers to the distance between crosslinking points illustrated in FIGS. 2A and 2B.

When the scattering length densities of the styrene-butadiene rubber and the deuterated toluene are the same in the model analysis, the below-described A is equal to B (A=B), specifically, $(0.62+8.39\ P_H P_N)\times 10^{10}=5.66\times 10^{10}$. Thus, $P_H P_N$ is calculated to be 0.60 (60%).
  A: Styrene-butadiene rubber: $(0.62+8.39\ P_H P_N)\times 10^{10}$ (cm$^{-2}$)
  B: Deuterated toluene: $5.66\times 10^{10}$ (cm$^{-2}$)

Then, $A_{DB}$ of 20.1 cm$^{-1}$ is obtained at a degree of $^1$H nuclear spin polarization of 60% at which the scattering length densities of the styrene-butadiene rubber and the deuterated toluene are the same.

Figure 3:
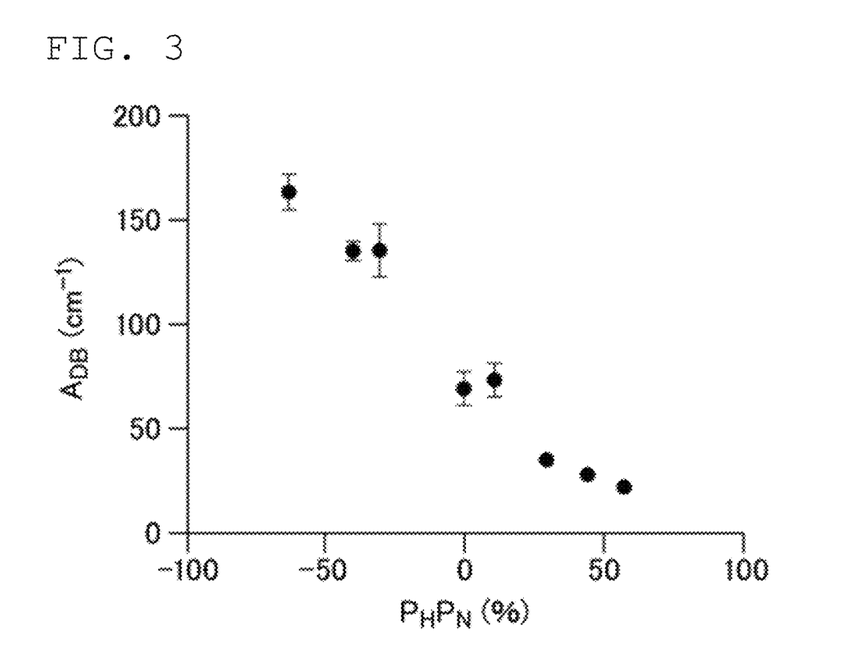
FIG. 3 shows a diagram showing a relationship between $P_H P_N$ and $A_{DB}$.

FIG. 3 shows a relationship between $P_H P_N$ and $A_{DB}$ obtained by the model analysis.

At the degree of polarization at which the scattering length densities of the styrene-butadiene rubber and the deuterated toluene are the same, the concentration of sulfur in the cross-linked rubber is a factor to cause contrast difference. Thus, the concentration of sulfur $\varphi_{sulfur}$ in the densely cross-linked part and the volume fraction $\varphi_1$ of the densely cross-liked part are calculated from $A_{DB}$ based on the following Expressions (2) to (5):

$$A_{DB}=\varphi_1(1-\varphi_1)(\Delta\rho)^2(8\pi\Xi^3) \quad (2)$$

$$(\Delta\rho)^2=\varphi_{sulfur}^2(\rho_{sulfur}-\rho_{SBR})^2 \quad (3)$$

$$\rho_{sulfur}=1.08\times 10^{10}\ [cm^{-2}] \quad (4)$$

$$\varphi_{sulfur,net}=\varphi_1\varphi_{sulfur} \quad (5)$$

where Ξ denotes the size of a densely cross-linked part, $\varphi_{sulfur}$ denotes the concentration of sulfur in the densely cross-linked part, and $\varphi_1$ denotes the volume fraction of the densely cross-linked part.

The values of $\rho_{SBR}$, $\rho_{d\text{-}toluene}$, $P_H P_N$, and $\varphi_{sulfur,net}$ are as follows.

$\rho_{SBR} = \rho_{d\text{-}toluene} = 5.66 \times 10^{10}$ [cm$^{-2}$]

$P_H P_N = +0.6$ $\varphi_{sulfur,net}$: volume fraction (charged amount) of sulfur = 0.0068

Table 1 shows the size Ξ (nm) of the densely cross-linked part, the size ξ (nm) of the cross-linked network, the volume fraction $\varphi_1$ of the densely cross-linked part, and the concentration of sulfur $\varphi_{sulfur}$ in the densely cross-linked part, which are determined by the above-described methods, in the measurement sample containing styrene-butadiene rubber, sulfur, etc.

TABLE 1

| | |
|---|---|
| Size Ξ (nm) of densely cross-linked part | 15 |
| Size ξ (nm) of cross-linked network | 0.9 |
| Volume fraction $\varphi_1$ of densely cross-linked part | 0.29 |
| Concentration of sulfur $\varphi_{sulfur}$ in densely cross-linked part | 0.023 |

For a comparison with the above-described evaluation method, an exemplary method without small-angle neutron scattering with $^1$H dynamic nuclear spin polarization is described below.

A measurement sample is prepared by introducing a paramagnetic radical compound and a deuterated solvent to the sample prepared in (Preparation of sample) described above by the following method.

Preparation of Solution Mixture

A deuterated toluene and toluene are mixed at predetermined ratios (10:0, 3:7, 5:5, 7:3, 0:10) to obtain solution mixtures.

Introduction of Paramagnetic Radical Compound and Deuterated Solvent

The sample and each solution mixture are placed in a vial such that the sample is completely immersed in the solution mixture, followed by standing still all day and night (about one day). Thus, the solution mixture is introduced into the sample, thereby obtaining a measurement sample.

Next, the measurement sample is subjected to SANS measurement using IBARAKI materials design diffractometer (iMATERIA) in J-PARC.

The data of an empty cell is subtracted from the measured scattering intensity, and then the size Ξ of the densely cross-linked part and the size ξ of a cross-linked network are obtained by Expression (1) as shown in Table 2. However, the volume fraction $\varphi_1$ of the densely cross-linked part and the concentration of sulfur $\varphi_{sulfur}$ in the densely cross-linked part cannot be obtained.

TABLE 2

| | |
|---|---|
| Size Ξ (nm) of densely cross-linked part | 15 |
| Size ξ (nm) of cross-linked | 0.9 |

TABLE 2-continued

| | |
|---|---|
| network | |
| Volume fraction $\varphi_1$ of densely cross-linked part | — |
| Concentration of sulfur $\varphi_{sulfur}$ in densely cross-linked part | — |

The results in Tables 1 and 2 sufficiently demonstrate the effectiveness of the method of evaluating the concentration of sulfur of the present disclosure.

The above-described method is an example using a polymer composite material containing styrene-butadiene rubber and sulfur. The evaluation can also be performed by the same technique while replacing the styrene-butadiene rubber with a different rubber component such as natural rubber, polyisoprene rubber, or polybutadiene rubber or using styrene-butadiene rubber together with a different rubber component.

The amounts of components in the polymer composite material (measurement sample), such as rubber components, sulfur, and fillers, are not limited and may be appropriately selected. For example, when samples to be analyzed are tire components, the amounts of components known for each tire component may be appropriately selected.

Non-limiting examples of tire components include a tread (cap tread, base tread), a belt layer, a sidewall, a bead apex, a clinch apex, an innerliner, an under tread, a breaker topping, and a ply topping.

Exemplary embodiments of the present disclosure include the following.

Embodiment 1: A method of evaluating a concentration of sulfur in a polymer composite material by small-angle neutron scattering with $^1$H dynamic nuclear spin polarization.

Embodiment 2: The method of evaluating a concentration of sulfur in a polymer composite material according to Embodiment 1 for evaluating a sulfur concentration $\varphi_{sulfur}$ in a densely cross-linked part of a polymer composite material.

Embodiment 3: The method of evaluating a concentration of sulfur in a polymer composite material according to Embodiment 1 or 2 for evaluating a volume fraction $\varphi_1$ of a densely cross-linked part of a polymer composite material.

Embodiment 4: The method of evaluating a concentration of sulfur in a polymer composite material according to any combination with any one of Embodiments 1 to 3, wherein the polymer composite material includes a paramagnetic radical compound and a deuterated solvent introduced therein.

Embodiment 5: The method of evaluating a concentration of sulfur in a polymer composite material according to Embodiment 4, wherein the paramagnetic radical compound is 2,2,6,6-tetramethylpiperidine 1-oxyl.

Embodiment 6: The method of evaluating a concentration of sulfur in a polymer composite material according to Embodiment 4 or 5, wherein the deuterated solvent is deuterated toluene.

Embodiment 7: The method of evaluating a concentration of sulfur in a polymer composite material according to any combination with any one of Embodiments 1 to 6, wherein the polymer composite material has a degree of $^1$H nuclear spin polarization of 50% or higher.

The invention claimed is:

1. A method of evaluating a concentration of sulfur in a polymer composite material by small-angle neutron scattering with 1H dynamic nuclear spin polarization, the method comprising:
    subjecting the polymer composite material to the small-angle neutron scattering with 1H dynamic nuclear spin polarization.

2. The method of evaluating a concentration of sulfur in a polymer composite material according to claim 1, further comprising evaluating a sulfur concentration φsulfur in a first cross-linked part of the polymer composite material, the first cross-linked part having a density of cross-linking that is higher than a second cross-linked part of the polymer composite material.

3. The method of evaluating a concentration of sulfur in a polymer composite material according to claim 1, further comprising evaluating a volume fraction φ1 of a first cross-linked part of the polymer composite material, the first cross-linked part having a density of cross-linking that is higher than a second cross-linked part of the polymer composite material.

4. The method of evaluating a concentration of sulfur in a polymer composite material according to claim 1,
    wherein the polymer composite material comprises a paramagnetic radical compound and a deuterated solvent introduced therein.

\* \* \* \* \*